United States Patent [19]
Baumann et al.

[11] Patent Number: 5,897,990
[45] Date of Patent: Apr. 27, 1999

[54] ASSAYS FOR MEASURING IMMUNOSUPPRESSANTS BY REPORTER GENE EXPRESSION

[75] Inventors: Goetz Baumann, Inzlingen, Germany; Franco E. Di Padova, Birsfelden, Switzerland; Peter Wenner, Lörrach, Germany

[73] Assignee: Novartis AG, Basel, Switzerland

[21] Appl. No.: 08/716,146

[22] PCT Filed: Mar. 17, 1995

[86] PCT No.: PCT/EP95/01009

§ 371 Date: Sep. 17, 1996

§ 102(e) Date: Sep. 17, 1996

[87] PCT Pub. No.: WO95/25812

PCT Pub. Date: Sep. 28, 1995

[30] Foreign Application Priority Data

Mar. 18, 1994 [GB] United Kingdom .................... 9405350

[51] Int. Cl.$^6$ .............................. C12N 5/10; C12N 15/11; C12Q 1/68; G01N 33/487

[52] U.S. Cl. ................................ 435/6; 435/8; 435/69.52; 435/69.8; 530/351; 530/413; 536/24.1; 536/23.2; 536/23.4; 536/23.5

[58] Field of Search ................................ 435/4, 6, 69.52, 435/69.8, 8; 530/351, 413; 536/23.2, 23.4, 23.5, 24.1

[56] References Cited

U.S. PATENT DOCUMENTS

5,350,574   9/1994   Erlanger et al. ............................ 514/9

FOREIGN PATENT DOCUMENTS

519336   12/1992   European Pat. Off. .
9304203   3/1993   WIPO .
9325712   12/1993   WIPO .
9409010   4/1994   WIPO .

OTHER PUBLICATIONS

Brombacher et al., IL–2 promoter–driven lacZ expression as a monitoring tool for IL–2 expression in primary T cells of transgenic mice, International Immunol., 6(2): 189–197, Feb. 1994.

Shan et al., The effect of rapamucin on c–jun expression in human lymphocytes, Clin. Immunol. Immunopathol., 69(3): 314–317, Dec. 1993.

Ganong, W.F., Review of Medical Physiology, Appleton & Lange:Norwalk, CT, p. 445, 1989.

Williams et al., "Advantages of Firefly Luciferase as a Reporter Gene: Application to the Interleukin–2–Gene Promoter", Anal. Biochem, vol. 176, pp. 28–32.

Hall et al., "Expression and Regulation of *Escherichia Coli* LacZ Gene Fusions in Mammalian Cells", J. Mol. Appl. Genetics, vol. 2, No. 1, pp. 101–109.

Dumont et al., "Distinct Mechanisms of Suppression of Murine T–cell Activation by the Related Macrolides FK–506 and Rapamycin", J. Immunology, vol. 144, No. 1, (Jan. 1, 1990).

Derwent Abstract 95–007479 of WPIDS document DE 4317577, Dec. 12, 1994.

*Primary Examiner*—Lorraine Spector
*Assistant Examiner*—Claire M. Kaufman
*Attorney, Agent, or Firm*—Diane E. Furman

[57] ABSTRACT

Quantitative reporter gene assays allowing for highly precise measurements of immunosuppressants in bodily fluids are provided, e.g., an IL-2 reporter gene assay for measuring blood levels of immunosuppressive cyclosporins and ascomycins (e.g., cyclosporin A and FK-506), and a c-jun reporter gene assay for measuring blood levels of immunosuppressive rapamycins.

20 Claims, 5 Drawing Sheets

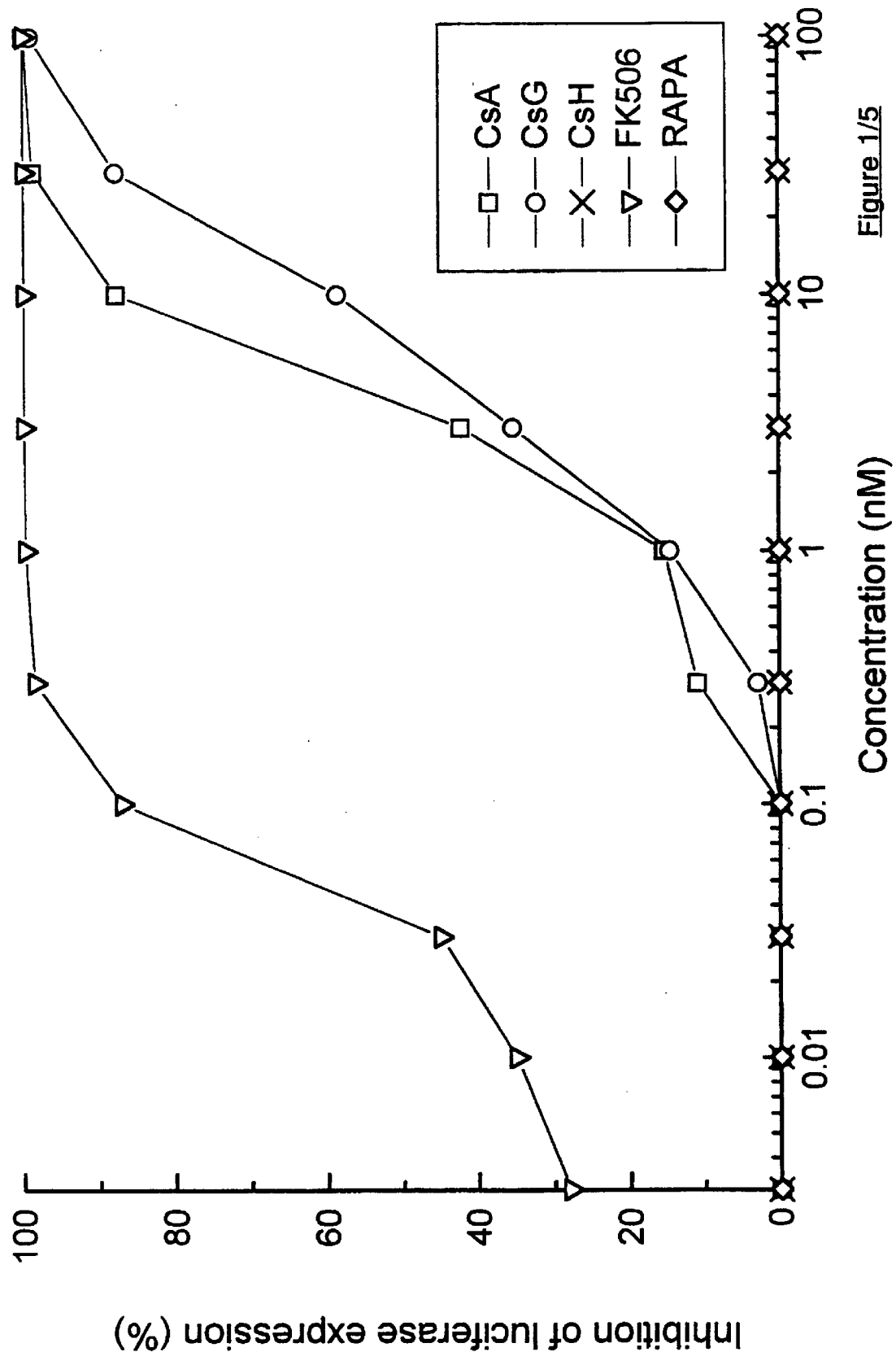
Figure 1/5

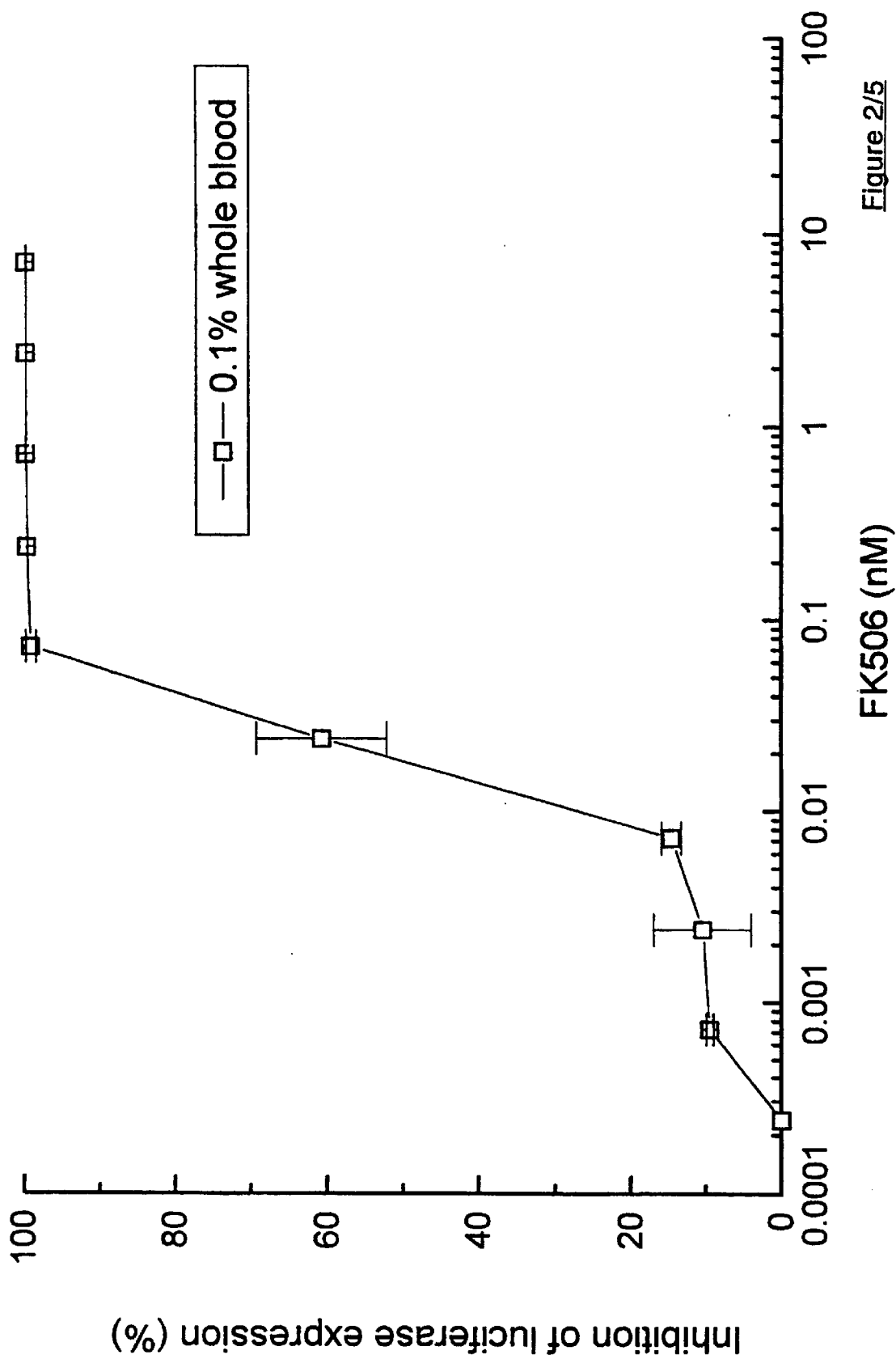
Figure 2/5

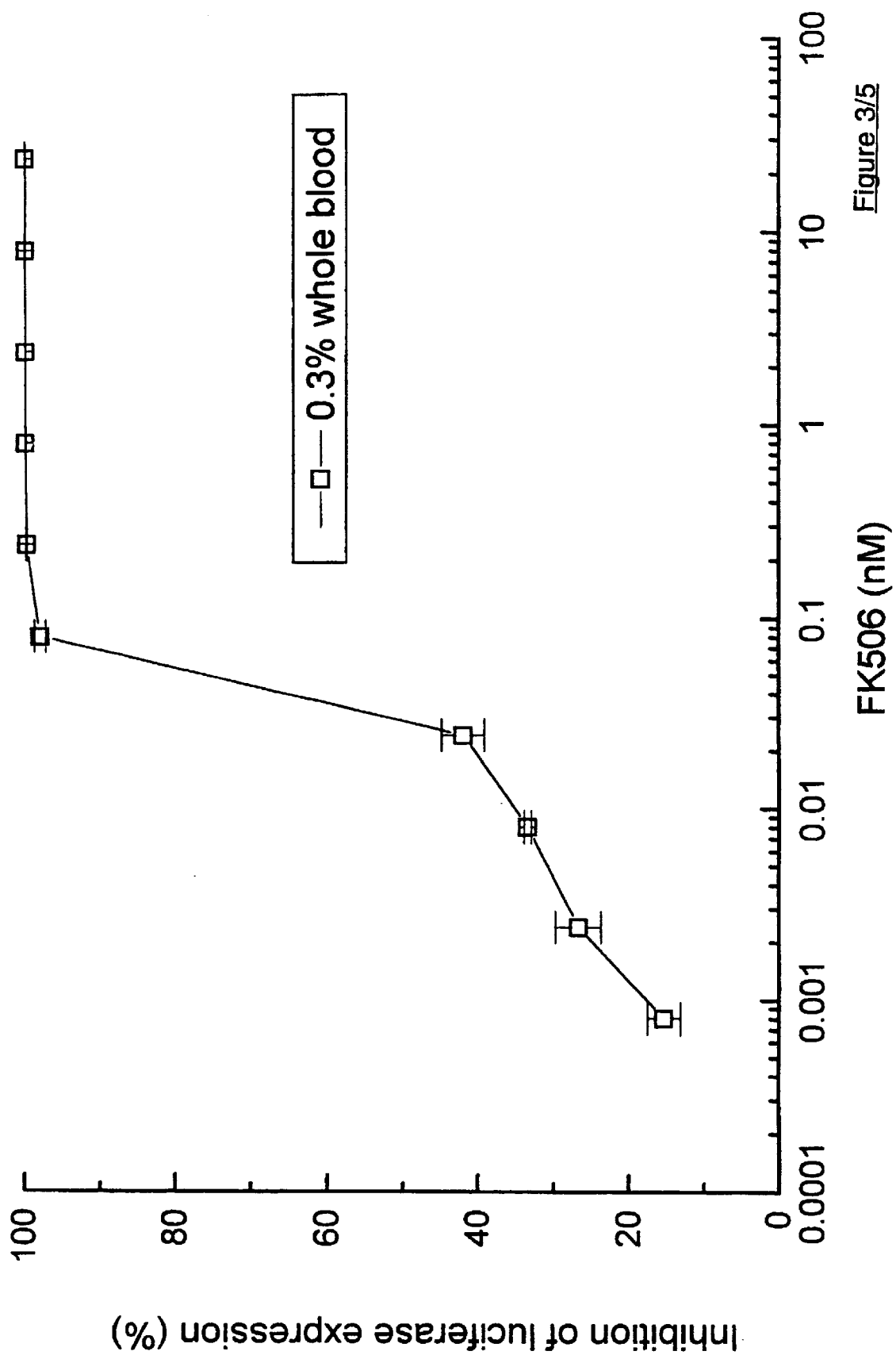
Figure 3/5

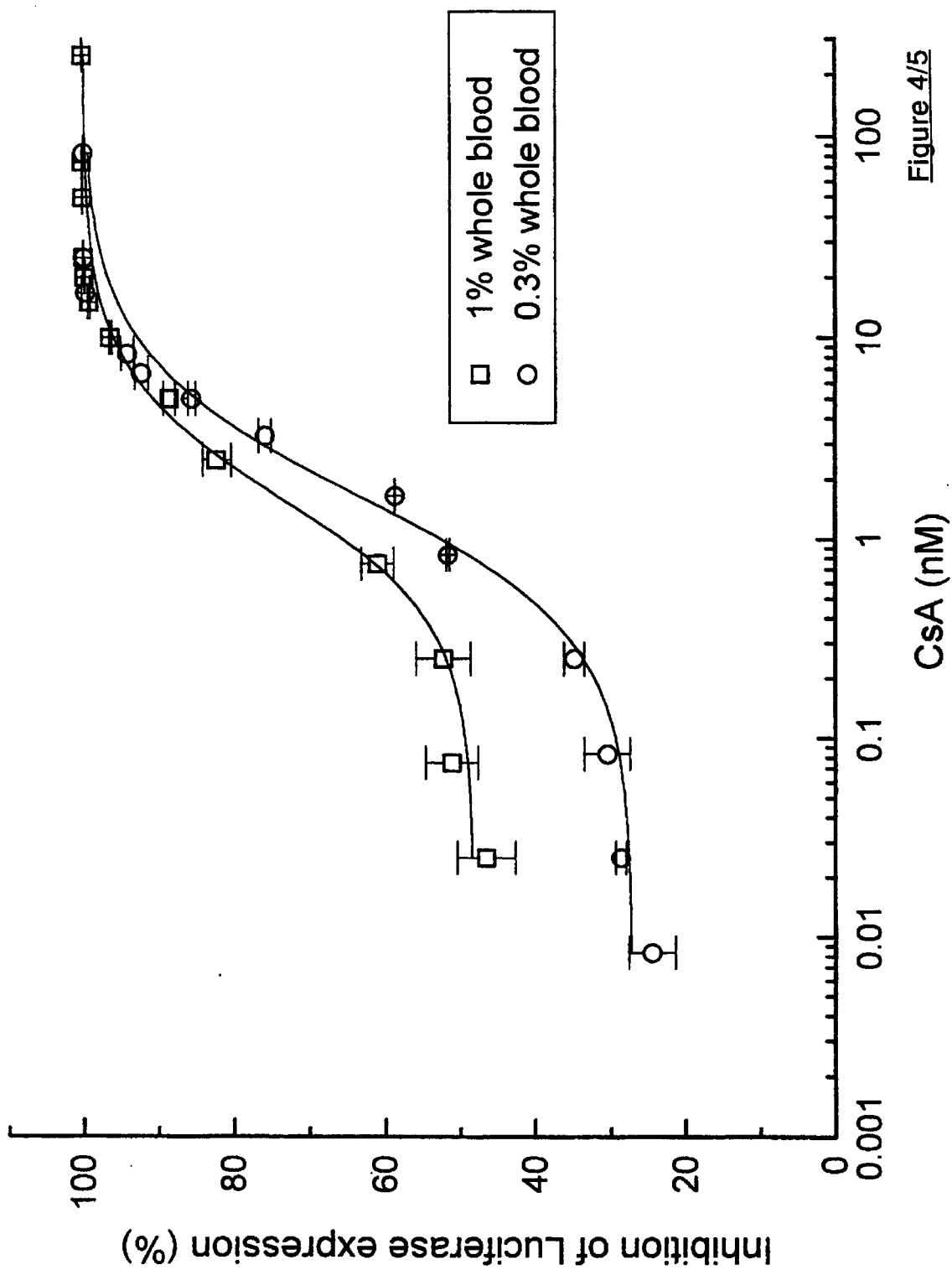

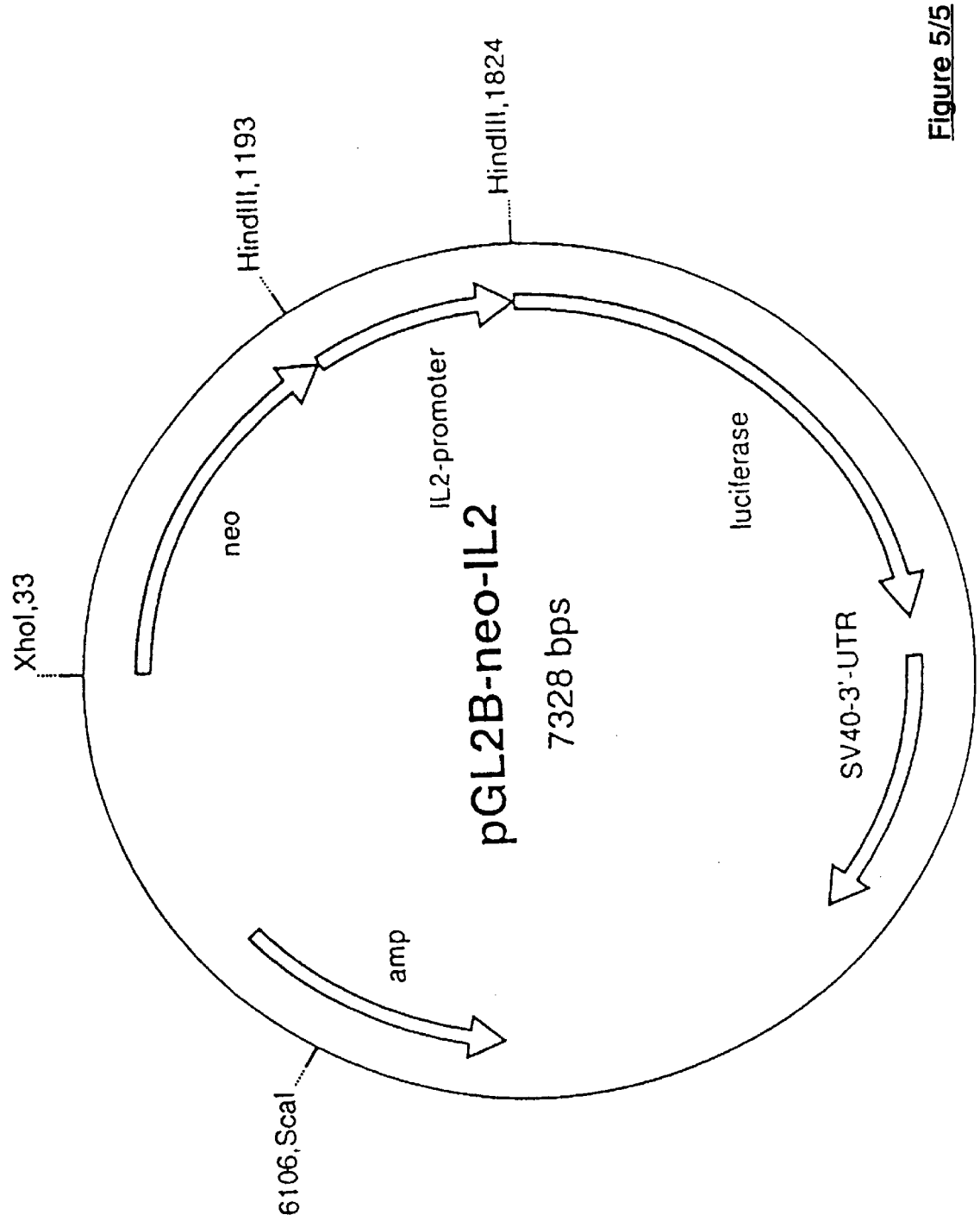
Figure 5/5

ASSAYS FOR MEASURING IMMUNOSUPPRESSANTS BY REPORTER GENE EXPRESSION

BACKGROUND OF THE INVENTION

This invention relates to new assay methods for monitoring the concentration in bodily fluids of immunosuppressants affecting gene expression, e.g., cyclosporins, such as cyclosporin A or cyclosporin G; ascomycins, such as FK-506; and rapamycins, e.g., rapamycin; using a reporter gene assay, e.g., an IL-2 reporter gene assay for immunosuppressive cyclosporins and ascomycins, or a c-jun reporter gene assay for immunosuppressive rapamycins.

Cyclosporins comprise a class of structurally distinct, cyclic, poly-N-methylated undecapeptides, generally possessing immunosuppressive, anti-inflammatory, anti-viral and/or anti-parasitic activity, each to a greater or lesser degree. The first of the cyclosporins to be identified was the fungal metabolite Cyclosporin A, or Ciclosporin, and its structure is given in The Merck Index, 11 th Edition; Merck & Co., Inc.; Rahway, N.J., USA (1989) under listing 2759. Later cyclosporins to be identified are cyclosporins B, C, D and G which are also listed in the Merck Index under listing 2759. A large number of synthetic analogues are also known and representative examples are disclosed in EP 296 123, EP 484 281, and GB 2222770. Cyclosporin A and its structurally similar analogues and derivatives are generally referred to as "cyclosporins" for the purposes of this specification.

Rapamycin is a macrolide immunosuppressant that is produced by *Streptomyces hygroscopicus* and which has been found to be pharmaceutically useful in a variety of applications, particularly as an immunosuppressant for use in the treatment and prevention of organ transplant rejection and autoimmune diseases. The structure of rapamycin is given in Kesseler, H., et al.; 1993; *Helv. Chim. Acta;* 76: 117. Large numbers of derivatives of rapamycin have been synthesized, including for example 40-O-alkylated derivatives such as 40-O-(2-hydroxy)ethyl-rapamycin (WO 94/09010), certain acyl and aminoacyl-rapamycins (e.g., U.S. Pat. No. 4,316,885, U.S. Pat. No. 4,650,803, and U.S. Pat. No. 5,151,413), 27-desmethyl-rapamycin (WO 92/14737), 26-dihydro-rapamycin (U.S. Pat. No. 5,138, 051), certain pyrazole derivatives (U.S. Pat. No. 5,164,399), certain alkoxyester derivatives (U.S. Pat. No. 5,233,036), and numerous others. Rapamycin and its structurally similar analogues and derivatives are termed collectively as "rapamycins" in this specification.

Ascomycins, of which FK-506 is the best known, are another class of generally immunosuppressive macrolides. FK506 is a macrolide immunosuppressant that is produced by *Streptomyces tsukubaensis* No 9993. The structure of FK506 is given in the appendix to the Merck Index, as item A5. A large number of related compounds which retain the basic structure and immunological properties of FK506 are also known. These compounds are described in various publications, for example EP 184162, EP 315973, EP 323042, EP 423714, EP 427680, EP 465426, EP 474126, WO 91/13889, WO 91/19495, EP 484936, EP 532088, EP 532089, WO 93/5059 and the like. Ascomycin, FK-506 and their structurally similar analogues and derivatives are termed collectively "ascomycins" in this specification.

Due to their extremely useful pharmaceutical properties, cyclosporins (Cyclosporins A and G in particular), rapamycins (e.g., rapamycin and 40-O-(2-hydroxy)ethyl-rapamycin) and ascomycins (e.g., FK-506) have wide application in, for example the prevention of transplant rejection and in the treatment of auto-immune diseases. However these compounds have side effects at higher doses and therefore their concentration in the blood must be kept within certain therapeutic ranges. Bioavailabilities and metabolic conversion rates tend to be patient specific and hence dosaging is patient specific. It is thus desirable to monitor the blood levels of such drugs and to adjust the dosage to obtain optimum blood levels of the drug thereby maximizing immunosuppression and minimizing adverse side effects.

Up until now, the method of choice for measuring blood levels of immunosuppressants has been using immunoassays with monoclonal antibodies (MAbs) specific for the immunosuppressants to be tested, or when mAb assays have not been available or practical, using HPLC. The immunoassay method has several very important drawbacks. First, different MAbs have different levels of affinity to the immunosuppressants and to their metabolites. Thus, it is difficult to make meaningful comparisons of data obtained by clinicians using different MAbs. Second, MAbs cannot distinguish between pharmacologically active and pharmacologically inactive metabolites. For example, a MAb that is very specific for the parent drug may not bind to a pharmacologically active metabolite and would thus understate the blood levels of immunosuppressant and lead to a serious risk of overdosage. On the other hand, a less specific MAb binds pharmacologically inactive metabolites as well as active metabolites, thus overstating the blood levels of immunosuppressant. HPLC likewise provides no information as to the immunosuppressive versus nonimmunosuppressive metabolite levels, and it is furthermore a relatively time-consuming and difficult method.

The problems with immunoassay methods have been particularly acute in the case of FK-506. A large contribution of the immunosuppressive activity of FK-506 derives not from FK-506 Per se, but from various unidentified immunosuppressive metabolites of FK-506. For example, it was recently reported in a study of thirteen transplant patients, that the ratio between FK-506 and one of its unidentified immunosuppressive metabolites detectable by HPLC was 1:10 in blood serum. Moreover, the metabolism of FK-506 is very erratic and highly variable from patient to patient. Finally, because of the very high potency of FK-506, it is necessary to achieve accurate measurements of the drug at extremely low concentrations, e.g., low nanomolar and sub-nanomolar concentrations. Commentators have pointed out the wide variability between observed levels of FK-506 using various immunoassays and the need to develop more reliable and consistent assays.

There is thus a clear and unfulfilled need to provide a monitoring system capable of accurately detecting blood levels of immunosuppressant drugs and their pharmacologically active metabolites. The present invention meets that need by providing a simple and sensitive method of monitoring blood levels of immunosuppressant using a reporter gene assay. The assay system can be applied to measure concentrations of any drug that influences expression of a gene in a dose dependant manner, but has been found to be particularly sensitive to and suitable for measuring concentrations of ascomycins, especially FK-506.

Although some reporter gene assays have been previously described in the literature, the use of such assays for diagnostic assays is new and inventive, particularly as it was not previously shown that the degree of inhibition of the assay could be correlated with the concentration of immunosuppressant sufficiently closely to permit highly accurate measurements of subnanomolar concentrations of immunosuppressants, thereby filling the long felt need for accurate measurement of very small concentrations of immunosuppressive substances in bodily fluids.

BRIEF DESCRIPTION OF THE DRAWINGS

FIG. 1 Standard curves for cyclosporin A (CsA), cyclosporin G (CsG), cyclosporin H (CsH), FK-506 (FK506) and rapamycin (RAPA) in luciferase IL-2 reporter gene assay.

FIG. 2 Standard curve for FK-506 concentration in whole blood diluted to 0.1% in luciferase IL-2 reporter gene assay.

FIG. 3 Standard curve for FK-506 concentration in whole blood diluted to 0.3% in luciferase IL-2 reporter gene assay.

FIG. 4 Standard curve for CsA concentration in whole blood diluted to 1% or 0.3% in luciferase IL-2 reporter gene assay.

FIG. 5 Plasmid pGL2B-neo-IL2 comprising luciferase gene under control of human IL-2 promoter, and neomycin resistance gene.

SUMMARY OF THE INVENTION

In the reporter gene assay used in the method of the invention, a chimeric gene construct is created comprising a reporter gene under the transcriptional control of a human promoter gene for a cytokine influenced by the immunosuppressant to be monitored, and this construct is incorporated into a suitable cell line. The cell line is preferentially a human T-cell or macrophage cell line, e.g., a Jurkat cell line, preferably selected for high native production of the desired gene product, for example producing IL-2 in response to stimulation in the case of an IL-2 reporter gene assay. The reporter gene is any gene expressing a readily observable product, e.g., an enzyme marker such as β-galactosidase or luciferase, or any other suitable enzyme marker. For example, where the enzyme marker is β-galactosidase, the reporter gene is, e.g., a bacterial lacZ gene; where the enzyme marker is luciferase, the gene is , e.g., a Phorinus luciferase gene. Another suitable marker is the gene for the green fluorescent protein produced by the bioluminescent jellyfish, e.g., as described in Chalfie, et al., *Science* (1994) 263: 802–805. The promoter gene is a promoter gene for a cytokine or protein for which transcription is stimulated or suppressed by the drug to be monitored. For example, where the drug to be monitored is a cyclosporin or FK-506, the promoter gene can be a promoter gene for mammalian IL-2, TGF-β, IFN-γ, or IL-4, as it has been found that these drugs inhibit gene expression of these cytokines in mammals. Preferably where the drug to be assayed is a cyclosporin or an ascomycin, e.g., cyclosporin A or G, or FK-506, the promotor gene is the promoter for human IL-2.

Where the drug to be monitored is rapamycin, the promoter gene is preferably the promoter for the mammalian proto-oncogene c-jun, as it has been found that rapamycin inhibits gene expression of c-jun in mammals. See, e.g., Shan, et al., *Clinical Immunology and Immunopathology* (1993) 69: 314–317.

Blood samples from the patient are diluted, their effect on gene expression in the above described system is measured, and the assay is standardized using known concentrations of the immunosuppressive material. Standard curves for FK-506, cyclosporin A and cyclosporin G using the luciferase IL-2 reporter gene assay are shown in FIG. 1. Rapamycin, a potent immunosuppressant having a structure somewhat resembling that of FK-506 but having no effect on IL-2 expression, and cyclosporin H, a nonimmunosuppressive cyclosporin, are included as controls. Standard curves for FK-506 concentration in whole blood samples diluted to 0.1% and 0.3% as measured by the luciferase IL-2 reporter gene assay are shown in FIGS. 2 and 3 respectively. As these curves demonstrate, the inhibition of gene expression is dose dependent at low concentrations, and FK-506, for example, can be measured at concentrations of less than 0.01 ng/ml using this system. Standard curves for cyclosporin A (CsA) concentration in whole blood diluted to 1% and 0.3% as measured by the luciferase IL-2 reporter gene assay are shown in FIG. 4. As in the case of FK-506, inhibition of IL-2 gene expression by cyclosporin A is dose dependent at low concentration, such that cyclosporin A concentrations can also be detected at sub nanomolar levels.

In a further embodiment of the invention, where a patient is receiving a combination of immunosuppressant drugs, the reporter gene assay method can be targeted to a particular immunosuppressant by removal or inhibition of other immunosuppressants using specific affinity separation techniques, e.g. utilizing specific antibodies (polyclonal or monoclonal, preferably monoclonal) or specific receptors to such immunosuppressants (e.g., cyclophilin for cyclosporin, FKBP-12 for FK-506 or rapamycin, or specific receptors for corticosteroids) and then measuring the remaining immunosuppressant. In particular, when patients are treated with combinations of corticosteroids and IL-2 gene suppressing immunosuppressant drugs such as FK-506 or cyclosporin A, it is desirable first to remove the corticosteroids. For example, where a patient, e.g., an organ transplant recipient, is receiving FK-506 or cyclosporin A and in addition a corticosteroid, e.g., prednisone, the FK-506 or cyclosporin level can be measured by taking blood from the patient, contacting the blood with beads coated with monoclonal antibody for prednisone, and then separating the blood from the beads, measuring the suppression of IL-2 gene expression in an IL-2 reporter gene assay in the presence of the blood, and comparing the level of suppression to that observed in the presence of known concentrations of FK-506 or cyclosporin. Other drugs which may be used in combination with cyclosporins or ascomycins, e.g., azathioprine, brequinar, desoxysperguailine, and rapamycins, do not affect the IL-2 reporter gene assay at therapeutic, e.g., low nanomolar, concentrations, and therefore need not be removed.

Ascomycins and rapamycins, including FK-506 and rapamycins, bind to macrophilins in the cells (e.g., FK-binding protein or FKBP-12), and cyclosporins bind to cyclophilins. These compounds may be freed from their respective immunophilins by treatment with an excess of a non-immunosuppressive, immunophilin binding competitor or by denaturing the immunophilin, e.g., by heat-treatment. Examples of nonimmunosuppressive, cyclophilin-binding cyclosporins suitable for use as binding competitors for immunosuppressive cyclosporins are described in EPA 484 281. Examples of nonimmunosuppressive, macrophilin-binding macrolides suitable for use as binding competitors for immunosuppressive macrolides such as rapamycins and ascomycins are described in WO 94/18207.

We note that, subsequent to the priority date of this application, certain aspects of the invention were published by one of the inventors in his doctoral thesis. See, Doctoral Dissertation by Wenner, P. (1994) "Entwicklung eines biologischen Testsystems zur Quantifizierung immunsuppressiver Substanzen in Körperflüssigkeiten" ("Development of a biological assay system for the quantification of immunosuppressive substances in bodily fluids"), Technischen Universität Carolo-Wilhelmina zu Braunschweig, Braunschweig, Germany. Reference to this thesis is suggested should further details of the background and the test system be desired.

In summary, the invention provides:

A method for measuring ex vivo the concentration of an immunosuppressant in bodily fluids, e.g., whole blood, comprising the step of quantitatively assaying the degree to which said bodily fluid is capable of inhibiting or promoting gene expression as measured in a reporter gene assay; e.g., a method of measuring the concentration of an immunosuppressive ascomycin or cyclosporin (e.g., FK-506 or cyclosporin A) in bodily fluids, e.g., whole blood, comprising the step of quantitatively assaying the degree to which the bodily fluid is capable of inhibiting gene expression of IL-2 as measured in an IL-2 reporter gene assay; or a method of measuring the concentration of an immunosuppressive rapamycin (e.g., rapamycin or 40-O-alkylated rapamycin) in bodily fluids, e.g., whole blood, comprising the step of quantitatively assaying the degree to which the blood is capable of inhibiting gene expression of c-jun as measured in a c-jun reporter gene assay;

said method optionally further comprising the step of first removing a selected immunosuppressant (e.g., a corticosteroid or second immunosuppressive drug) from the bodily fluid to be assayed using selective affinity separation; and/or optionally further comprising a step wherein an immunophilin-binding immunosuppressant (e.g., a cyclosporin, an ascomycin, or a rapamycin) is first released from a complex with an immunophilin (e.g., in the case of an ascomycin or a rapamycin, the immunophilin being a macrophilin, e.g., FKBP-12, and in the case of a cyclosporin, the immunophilin being cyclophilin), e.g., by treatment of the bodily fluid with an excess of a nonimmunosuppressive, immunophilin-binding compound, or by incubation of the bodily fluid, e.g., at temperatures substantially in excess of body temperature, e.g., 45–95° C., preferably 50–60° C.; and/or optionally further comprising a step wherein the bodily fluid is diluted, e.g., with distilled water, e.g., to a concentration less than 5%, preferably 0.1–1%.

The invention further provides an assay kit suitable for carrying out any of these methods, e.g., An assay kit for measuring the concentration of an immunosuppressant in bodily fluids, e.g., whole blood, comprising a suitable cell line, e.g., a cell line stimulation of which can be suppressed by the immunosuppressant to be measured, (e.g., a T-cell clone, e.g., a Jurkat clone) transfected with a reporter gene (e.g., a marker gene such as beta-galactosidase or luciferase) under the control of a promoter gene (e.g., a promotor for a cytokine or protein the expression of which is suppressed by the immunosuppressant to be measured); e.g., an assay kit wherein the promoter gene is a promotor gene for human IL-2 and the reporter gene is bacterial lacZ gene or Photinus luciferase gene, for measuring levels of an immunosuppressive ascomycin or cyclosporin (e.g., FK-506 or cyclosporin A) in whole blood;

said kit optionally further comprising standard samples of the immunosuppressant to be measured, e.g., samples of a predetermined concentration in an amount sufficient for use in standardizing the kit;

said kit optionally further comprising a compound having affinity for a selected immunosuppressant (e.g., a different immunosuppressant from the one to be measured, especially a corticosteroid);

said kit optionally further comprising a nonimmunosuppressive, immunophilin-binding cyclosporin or macrolide.

In a third embodiment, the invention provides a novel second use of a reporter gene assay as a quantitative measuring tool, e.g.

Use of a reporter gene assay to measure the level of an immunosuppressant in a bodily fluid ex vivo; e.g.

use of an IL-2 reporter gene assay to measure the level of an immunosuppressive ascomycin or cyclosporin (e.g., FK-506 or cyclosporin A) in whole blood.

EXAMPLE 1

β-Galatosidase IL-2 Reporter Gene Assay a. Preparation of T-cell Clones

The RsaI restriction fragment from position −583 to +40 of the human IL-2 promoter is amplified from genomic DNA (Clontech, #6550-2) by the polymerase chain reaction (PCR) using DNA primers with suitable HindIII restriction at either end. The amplified fragment is gel purified, digested with HindIII and subsequently cloned in the right orientation into the appropriate restriction site 5' to the start site of the lacZ translation in a plasmid containing the lacZ gene (placZH, supplied by L. Herzenberg, Stanford University) to give the plasmid pIL-2-lacZ, analogously to the method described in Norton, et al., Molecular and Cellular Biology (1985) 5: 281–290.

For β-galactosidase expression (encoded by the E. coli lacZ gene) in eukaryotic cells the initiation region of translation is derived from the Moloney murine leukemia virus envelope gene and the poly adenylation sequence from the small t intron of SV-40, e.g., as described in van Doren, et al., J. Virol. 50: 606 (1984). The DNA sequence of the amplified IL-2 promoter fragment and the fusion points are verified by sequencing after cloning. CsCl-purified DNA of pIL-2-lacZ is linearized for transfection with KpnI which cuts immediately 3' of the hygromycin resistance gene. $10^7$ Jurkat cells (e.g., Jurkat K16, clone 41-19) are electroporated in 1 ml serum-free RMPI medium with 20 μg of linearized pIL-2-lacZ, using a BioRad apparatus at 250 V and 960 μF as described, e.g., in Mattila, et al., EMBO J. 9: 4425 (1990).

The DNA manipulations described are carried out using standard methods, e.g., as described in Sambrook, et al. (eds.) *Molecular Cloning—A Lab Manual,* 2nd ed., (1989, Cold Spring Harbor Lab Press), and Ausubel, et al. (eds.) *Current Protocols in Molecular Biology* (1987, Wiley-Interscience, New York).

b. Ex vivo whole blood assay of IL-2 transcription suppressors

Cells as prepared in step a) may be used to detect the presence of compounds in bodily fluids which suppress IL-2 transcription. Mitogenic stimulation of these T-cells results in the parallel expression of endogenousIL-2 and β-galactosidase.

Expression of this enzyme is measured by the fluorescence generated on cleavage of its substrate, 4-methylumbelliferyl-β-D-galactoside (MUG, obtainable commercially, e.g., from Sigma). The presence and amount of immunosuppressive compounds which, like the immunosuppressive cyclosporins and ascomycins, exhibit dose-dependant suppression of IL-2 gene expression can thus be measured as inhibition of expression of β-galactosidase by the transfected cells.

To measure concentration of immunosuppressant in whole blood, EDTA whole blood samples from the patients are tested promptly or are promptly frozen and kept at −20° C. Aliquots of 200 µl freshly drawn or freshly thawed blood are heat-inactivated at 56° C. for 30 minutes and subsequently diluted to 3% with Medium C (i.e., Isocove's Modified Dulbecos Medium containing Albumin, Transferrin, and Lecithin (IMDM-ATL), e.g., as described in Schreier, et al., *Immunological Methods* (1981, Academic Press) vol. 2). Tests are performed in 96-well plates (Costar) with a total volume of 200 µl/well. Twenty µl of diluted blood are added to each well to a final concentration of 0.3%. At this concentration, only a minor inhibitory effect of blood components can be seen on the IL-2 reporter gene assay. Each sample is measured in quadruplicate. Five×$10^4$ cells (Jurkat pIL-2-lacZ transformed as described above) per well are stimulated with the mitogens phytohemagglutinin (PHA, 1 µg/ml) and phorbal 12-myristate 13-acetate (PMA, 20 ng/ml). After 16 hours of culture, the plates are centrifuged for 10 minutes (RCF=700). supernatants are removed and 180 µl of reaction buffer (100 mM $NaPO_4$, pH 9.0; 10 mM KCl; 0.1% Triton X-100; 0.5 mM MUG) is added to each well. Plates are then shaken for 10 minutes and after 2 hours incubation at 22° C. in the dark, fluorescence is measured (excitation-filter=360 nm, emission-filter=460 nm) on a CytoFluor 2300 fluorescence reader (Millipore).

EXAMPLE 2

Luciferase IL-2 Reporter Gene Assay a. Preparation of T-cell Clone

This IL-2 reporter-gene-assay (IL-2 RGA) also uses a chimeric gene construct which is stably integrated into a human leukemic T-cell line (e.g., Jurkat K16, clone 41-19) as described in the previous example. In this construct the luciferase gene from the American firefly *Photinus pyralis* (derived from pGL2-Basic vector E1614 available from Promega, Madison, Wis., USA) is put under the transcriptional control of the human IL-2 promotor in a vector also containing a neomycin resistance cartridge (derived from pMC1Neo Poly A vector 213201, available from Stratagene, LaJolla, Calif., USA) and introduced into the Jurkat cells as described in example 1 above. (A diagram of the transfection vector is shown in FIG. 5). Mitogenic stimulation of the transformed cells results not only in the endogenous expression of IL-2 but also of luciferase, whose enzymatic activity can be measured due to its ability to catalyze the oxidative decarboxylation of D-luciferin (i.e., D-luciferin sodium, available from Chemie Brunschwig AG) resulting in the production of light. This luminescence, which correlates directly with mitogen stimulated luciferase expression in the transformed cells, is quantified in a Luminoskan reader (Labsystems, Helsinki, Finland). Inhibition is expressed as a percentage of expression compared to a positive control (100%) where no test fluid is added to the stimulated cells. The test is standardized using known concentrations of immunosuppressant to obtain a graph correlating immunosuppressant concentration with level of IL-2 transcription inhibition. This luciferase IL-2 reporter gene assay is very sensitive to immunosuppressive substances affecting IL-2 transcription, with an $IC_{50}$ for cyclosporin A of ca. 2 ng/ml, and an $IC_{50}$ for FK-506 of <0.1 ng/ml.

b. Ex vivo whole blood assay of IL-2 transcription suppressors Whole blood samples are kept at −20° C. until they are tested. Immediately after thawing, aliquots of 100 µl are heat inactivated at 56° C. for 30 min and subsequently diluted to 3% or 10% with Medium C. Tests are performed in 96-well plates with a total volume of 200 µl/well. Twenty µl of diluted blood are added to each well to a final concentration of 0.3% or 1%. 5×$10^4$ cells/well in a total volume of 200 µl are mitogen-stimulated (PMA 40 ng/m+Ionomycin 2 µM) for 16 hours at 37° C. (5% $CO_2$). After stimulation plates are centrifuged for 10 minutes (700 rcf) and the supernatant removed. 20 µl of lysis buffer (25 MM Tris-phosphate (pH 7.8), 2 mM DTT, 2 mM 1.2-diaminocyclohexane-N,N,N', N-tetraacetic acid, 10% (v/v) glycerol and 1% (v/v) Triton X-100) is added to each well and the plates are shaken for 10 min. The plates are then placed in the Luminoskan reader where 50 µl of luciferase assay reaction buffer is automatically added to give a final concentration of 20 mM Tricine, 1.07 mM $(MgCO_3)_4$—$Mg(OH)_2$ -$5H_2O$, 2.67 mM $MgSO_4$, 0.1 mM EDTA, 33.3 DTT, 270 µM Coenzyme A, 470 µM Luciferin, 530 µM ATP, pH 7.8, and the luminescence is measured. All samples are measured in quadruplicate.

EXAMPLE 3

Removal of Corticosteroids

Plastic beads are coated with monoclonal antibody to prednisone (e., prepared as described in Kohler, et al., *Nature* (1975) 256: 49–51, using prednisone or other desired corticosteroid as immunogenic antigen co-injected with Freund's adjuvant). Blood samples from patients receiving FK-506 and prednisone are diluted in Medium C as described above and passed through a column containing such beads. Following removal of corticosteroids, the blood is assayed for the presence of remaining IL-2 transcription inhibitors as described in example 1 or 2, which will comprise FK-506 plus its immunosuppressive metabolites.

We claim:

1. A method for measuring ex vivo the concentration of an immunosuppressant or its pharmacologically active metabolites in a bodily fluid, wherein said immunosuppressant is a cyclosporin or ascomycin, comprising:

subjecting cells of a T-cell line transfected with a reporter gene under the control of an IL-2 promoter to conditions sufficient to stimulate IL-2 transcription, treating at least a portion of said cells with a bodily fluid diluted to a concentration of less than 5%, whereby expression of said reporter gene in a treated cell is inhibited relative to expression of said reporter gene in an untreated cell, and comparing the degree of inhibition of reporter gene expression effected by said bodily fluid with the degree of inhibition of reporter gene expression effected by a known concentration of the immunosuppressant, wherein said comparing indicates the concentration of said immunosuppressant or metabolite thereof in said bodily fluid.

2. A method for measuring ex vivo the concentration of an immunosuppressant or its pharmacologically active metabolites in a bodily fluid, wherein said immunosuppressant is a rapamycin, comprising:

subjecting cells of a T-cell line transfected with a reporter gene under the control of a c-jun promoter to conditions sufficient to stimulate c-jun transcription, treating at least a portion of said cells with a bodily fluid diluted to a concentration of less than 5%, whereby expression of said reporter gene in a treated cell is inhibited relative to expression of said reporter gene in an untreated cell, and comparing the degree of inhibition of reporter gene expression effected by said bodily fluid with the degree of inhibition of reporter gene expression effected by a known concentration of the immunosuppressant, wherein said comparing indicates the concentration of said immunosuppressant or metabolite thereof in said bodily fluid.

3. A method for measuring ex vivo the concentration of an immunosuppressant or its pharmacologically active metabolites in a bodily fluid, wherein said immunosuppressant is a cyclosporin, comprising:

subjecting cells of a T-cell line transfected with a reporter gene under the control of a promoter selected from the group consisting of promoters for the cytokines IL-2, TGF-β, IFN-γ and IL-4, under conditions sufficient to stimulate transcription of the cytokine, treating at least a portion of said cells with a bodily fluid diluted to a concentration of less than 5%, whereby expression of said reporter gene in a treated cell is inhibited relative to expression of said reporter gene in an untreated cell, and comparing the degree of inhibition of reporter gene expression effected by said bodily fluid with the degree of inhibition of reporter gene expression effected by a known concentration of the immunosuppressant, wherein said comparing indicates the concentration of said immunosuppressant or metabolite thereof in said bodily fluid.

4. The method of claim 1, 2, or 3 further comprising the step of first removing a selected immunosuppressant (other than the immunosuppressant to be measured) from the bodily fluid to be assayed using selective affinity separation.

5. A method according to claim 1 wherein the immunosuppressant is FK-506.

6. A method according to claim 5 wherein the bodily fluid is whole blood.

7. A method according to claim 1 wherein the immunosuppressant is cyclosporin A.

8. A method according to claim 7 wherein the bodily fluid is whole blood.

9. A method according to claim 2 comprising the step of first releasing the immunosuppressant from a complex with an immunophilin.

10. A method according to claim 3 wherein the immunosuppressant is cyclosporin A.

11. A method according to claim 10 wherein the bodily fluid is whole blood.

12. a method according to claim 3 wherein the immunosuppressant is a 40-O-alkylated rapamycin.

13. A method according to claim 12 wherein the bodily fluid is whole blood.

14. A method according to claim 12 wherein the 40-O-alkylated rapamycin is 40-O-(2-hydroxy)ethyl-rapamycin).

15. A method according to claim 14 wherein the bodily fluid is whole blood.

16. An assay kit for monitoring the concentration of an immunosuppressant in a bodily fluid comprising:

cells of a T-cell clone transfected with a reporter gene under the control of a promoter, said promoter being a promoter for a cytokine or protein the transcription of which is stimulated or suppressed in said cells by the immunosuppressant to be monitored, and one or more concentration standards of the immunosuppressant to be monitored, wherein
(a) the immunosuppressant is an ascomycin and the promoter is an IL-2 promoter, or
(b) the immunosuppressant is a cyclosporin and the promoter is selected from the group consisting of IL-2, TGF-β, IFN-γ, and IL-4 promoters, or
(c) the immunosuppressant is a rapamycin and the promoter is a c-jun promoter.

17. A kit according to claim 16 further comprising a compound having selectivity for an immunosuppressant different from the one to be measured.

18. A kit according to claim 16 further comprising a non-immunosuppressive, immunophilin-binding cyclosporin or macrolide.

19. An assay kit according to claim 16 where the promoter is a promotor for human IL-2 and the reporter gene is bacterial lacZ gene or Photinus luciferase gene, for measuring levels of an immunosuppressive ascomycin or cyclosporin in whole blood.

20. An assay kit according to either of claims 16 or 19 further comprising a compound having affinity for a selected immunosuppressant other than the immunosuppressant to be measured.

* * * * *